US012569595B2

(12) United States Patent
Tian et al.

(10) Patent No.: US 12,569,595 B2
(45) Date of Patent: Mar. 10, 2026

(54) BIOPROSTHETIC TISSUE PREPARATION

(71) Applicant: Edwards Lifesciences Corporation, Irvine, CA (US)

(72) Inventors: Bin Tian, Irvine, CA (US); Angela B. De La Fuente, San Clemente, CA (US); Gregory A. Wright, Orange, CA (US); Jingjia Han, Irvine, CA (US); Hao Shang, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 833 days.

(21) Appl. No.: 17/806,041

(22) Filed: Jun. 8, 2022

(65) Prior Publication Data

US 2022/0296779 A1     Sep. 22, 2022

Related U.S. Application Data

(63) Continuation of application No. PCT/US2020/063728, filed on Dec. 8, 2020.

(60) Provisional application No. 62/945,721, filed on Dec. 9, 2019.

(51) Int. Cl.
*A61L 33/00*     (2006.01)
*A61L 27/36*     (2006.01)

(52) U.S. Cl.
CPC ....... *A61L 27/3687* (2013.01); *A61L 2430/20* (2013.01)

(58) Field of Classification Search
None
See application file for complete search history.

(56) References Cited

U.S. PATENT DOCUMENTS

| | | | |
|---|---|---|---|
| 2,393,580 A | 1/1946 | Weiskopf | |
| 4,120,649 A | 10/1978 | Schechter | |
| 4,323,358 A | 4/1982 | Lentz et al. | |
| 4,350,492 A | 9/1982 | Wright et al. | |
| 4,372,743 A | 2/1983 | Lane | |
| 4,378,224 A | 3/1983 | Nimni et al. | |
| 4,402,697 A | 9/1983 | Pollock et al. | |
| 4,405,327 A | 9/1983 | Pollock | |
| 4,481,009 A | 11/1984 | Nashef | |
| 4,553,974 A | 11/1985 | Dewanjee | |
| 4,624,822 A | 11/1986 | Arru et al. | |
| 4,647,283 A | 3/1987 | Carpentier et al. | |

(Continued)

FOREIGN PATENT DOCUMENTS

| | | |
|---|---|---|
| CN | 103705980 A | 4/2014 |
| CN | 106390202 A | 2/2017 |

(Continued)

OTHER PUBLICATIONS

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.

(Continued)

*Primary Examiner* — Jyoti Nagpaul
(74) *Attorney, Agent, or Firm* — KPPB LLP

(57)     ABSTRACT

Methods for preparing bioprosthetic tissue are provided. In some instances, bioprosthetic tissue is treated to remove antigenic biomolecules. In some instances, prepared bioprosthetic tissues are incorporated into a medical device.

21 Claims, 3 Drawing Sheets

(56) References Cited

U.S. PATENT DOCUMENTS

| | | | |
|---|---|---|---|
| 4,648,881 A | 3/1987 | Carpentier et al. |
| 4,758,151 A | 7/1988 | Arru et al. |
| 4,770,665 A | 9/1988 | Nashef |
| 4,776,853 A | 10/1988 | Klement et al. |
| 4,786,287 A | 11/1988 | Nashef et al. |
| 4,838,888 A | 6/1989 | Nashef |
| 4,865,871 A | 9/1989 | Livesey et al. |
| 4,885,005 A | 12/1989 | Nashef et al. |
| 4,958,008 A | 9/1990 | Petite et al. |
| 4,976,733 A | 12/1990 | Girardot |
| 5,002,566 A | 3/1991 | Carpentier et al. |
| 5,051,401 A | 9/1991 | Sikes |
| 5,080,670 A | 1/1992 | Imamura et al. |
| 5,094,661 A | 3/1992 | Levy et al. |
| 5,104,405 A | 4/1992 | Nimni |
| 5,116,564 A | 5/1992 | Jansen et al. |
| 5,147,514 A | 9/1992 | Mechanic |
| 5,154,007 A | 10/1992 | Piunno et al. |
| 5,200,399 A | 4/1993 | Wettlaufer et al. |
| 5,215,541 A | 6/1993 | Nashef et al. |
| 5,279,612 A | 1/1994 | Eberhardt |
| 5,329,846 A | 7/1994 | Bonutti |
| 5,397,353 A | 3/1995 | Oliver et al. |
| 5,437,287 A | 8/1995 | Phillips et al. |
| 5,447,536 A | 9/1995 | Girardot et al. |
| 5,460,962 A | 10/1995 | Kemp |
| 5,476,516 A | 12/1995 | Seifter et al. |
| 5,509,932 A | 4/1996 | Keogh et al. |
| 5,558,875 A | 9/1996 | Wang |
| 5,595,571 A | 1/1997 | Jaffe et al. |
| 5,613,982 A | 3/1997 | Goldstein |
| 5,645,587 A | 7/1997 | Chanda et al. |
| 5,674,298 A | 10/1997 | Levy et al. |
| 5,697,972 A | 12/1997 | Kim et al. |
| 5,713,953 A | 2/1998 | Vallana et al. |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,766,520 A | 6/1998 | Bronshtein |
| 5,769,780 A | 6/1998 | Hata et al. |
| 5,782,914 A | 7/1998 | Schankereli |
| 5,782,931 A | 7/1998 | Yang et al. |
| 5,843,180 A | 12/1998 | Jaffe et al. |
| 5,843,181 A | 12/1998 | Jaffe et al. |
| 5,855,620 A | 1/1999 | Bishopric et al. |
| 5,862,806 A | 1/1999 | Cheung |
| 5,873,812 A | 2/1999 | Ciana et al. |
| 5,899,936 A | 5/1999 | Goldstein |
| 5,911,951 A | 6/1999 | Girardot et al. |
| 5,919,472 A | 7/1999 | Trescony et al. |
| 5,921,980 A | 7/1999 | Kirn |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,993,844 A | 11/1999 | Abraham et al. |
| 6,008,292 A | 12/1999 | Lee et al. |
| 6,017,741 A | 1/2000 | Keogh |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,375,680 B1 | 4/2002 | Carlyle |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Girardot et al. |
| 6,509,145 B1 | 1/2003 | Torrianni |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,589,591 B1 | 7/2003 | Mansouri et al. |
| 6,605,667 B1 | 8/2003 | Badejo et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,682,559 B2 | 1/2004 | Myers et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,872,226 B2 | 3/2005 | Cali et al. |
| 6,878,168 B2 | 4/2005 | Carpentier et al. |
| 6,908,591 B2 | 6/2005 | MacPhee et al. |
| 6,911,043 B2 | 6/2005 | Myers et al. |
| 6,919,172 B2 | 7/2005 | DePablo et al. |
| 7,008,763 B2 | 3/2006 | Cheung |
| 7,029,434 B2 | 4/2006 | Carpentier et al. |
| 7,037,333 B2 | 5/2006 | Myers et al. |
| 7,063,726 B2 | 6/2006 | Crouch et al. |
| 7,078,163 B2 | 7/2006 | Torrianni |
| 7,141,064 B2 | 11/2006 | Scott et al. |
| 7,143,769 B2 | 12/2006 | Stoltz et al. |
| 7,214,344 B2 | 5/2007 | Carpentier et al. |
| 7,238,200 B2 | 7/2007 | Lee et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,367,969 B2 | 5/2008 | Stoltz et al. |
| RE40,570 E | 11/2008 | Carpentier et al. |
| 7,498,565 B2 | 3/2009 | Silberberg et al. |
| 7,579,381 B2 | 8/2009 | Dove |
| 7,594,974 B2 | 9/2009 | Cali et al. |
| 7,648,676 B2 | 1/2010 | Mills et al. |
| 7,682,304 B2 | 3/2010 | Heyninck-Jantz et al. |
| 7,914,569 B2 | 3/2011 | Nguyen et al. |
| 7,919,112 B2 | 4/2011 | Pathak et al. |
| 7,972,376 B1 | 7/2011 | Dove et al. |
| 8,007,992 B2 | 8/2011 | Tian et al. |
| 8,038,708 B2 | 10/2011 | Case et al. |
| 8,043,450 B2 | 10/2011 | Cali et al. |
| 8,075,615 B2 | 12/2011 | Eberhardt et al. |
| 8,105,375 B2 | 1/2012 | Navia et al. |

(56) References Cited

U.S. PATENT DOCUMENTS

| | | | |
|---|---|---|---|
| 8,136,218 | B2 | 3/2012 | Millwee et al. |
| 8,308,797 | B2 | 11/2012 | Paniagua et al. |
| 8,361,144 | B2 | 1/2013 | Fish et al. |
| 8,377,143 | B2 | 2/2013 | Hamby et al. |
| 8,475,827 | B2 | 7/2013 | Hamby et al. |
| 10,383,978 | B2 | 8/2019 | Dong et al. |
| 10,722,613 | B2 | 7/2020 | Ashworth et al. |
| 2001/0000804 | A1 | 5/2001 | Goldstein et al. |
| 2001/0025196 | A1 | 9/2001 | Chinn et al. |
| 2001/0027344 | A1 | 10/2001 | Bonutti |
| 2001/0032024 | A1 | 10/2001 | Cunanan et al. |
| 2001/0039459 | A1 | 11/2001 | Stone |
| 2002/0001834 | A1 | 1/2002 | Keogh et al. |
| 2002/0091441 | A1 | 7/2002 | Guzik |
| 2002/0111532 | A1 | 8/2002 | Pathak et al. |
| 2003/0035843 | A1 | 2/2003 | Livesey et al. |
| 2003/0125805 | A1 | 7/2003 | Johnson et al. |
| 2003/0135284 | A1 | 7/2003 | Crouch et al. |
| 2003/0167089 | A1 | 9/2003 | Lane |
| 2003/0212454 | A1 | 11/2003 | Scott et al. |
| 2004/0030381 | A1 | 2/2004 | Shu |
| 2004/0086543 | A1 | 5/2004 | Keogh et al. |
| 2004/0158320 | A1 | 8/2004 | Simionescu et al. |
| 2005/0010773 | A1 | 1/2005 | Lapstun et al. |
| 2005/0119736 | A1 | 6/2005 | Zilla et al. |
| 2005/0136510 | A1 | 6/2005 | Hendriks et al. |
| 2005/0211680 | A1 | 9/2005 | Li et al. |
| 2006/0084957 | A1 | 4/2006 | Delfyett et al. |
| 2006/0099326 | A1 | 5/2006 | Keogh et al. |
| 2006/0110370 | A1 | 5/2006 | Pathak et al. |
| 2006/0159641 | A1 | 7/2006 | Girardot et al. |
| 2006/0193885 | A1 | 8/2006 | Leonard Neethling et al. |
| 2006/0210960 | A1 | 9/2006 | Livesey et al. |
| 2006/0217804 | A1 | 9/2006 | Dove |
| 2006/0217805 | A1 | 9/2006 | Dove |
| 2007/0050014 | A1 | 3/2007 | Johnson |
| 2007/0073392 | A1 | 3/2007 | Heyninck-Jantz et al. |
| 2007/0203576 | A1 | 8/2007 | Lee et al. |
| 2007/0254005 | A1 | 11/2007 | Pathak et al. |
| 2008/0302372 | A1 | 12/2008 | Davidson et al. |
| 2008/0319166 | A1 | 12/2008 | Shen |
| 2009/0041729 | A1 | 2/2009 | Wolfinbarger, Jr. et al. |
| 2009/0130162 | A2 | 5/2009 | Pathak et al. |
| 2009/0137999 | A1 | 5/2009 | Silberberg et al. |
| 2009/0188900 | A1 | 7/2009 | Cali et al. |
| 2009/0326524 | A1 | 12/2009 | Cali et al. |
| 2010/0036484 | A1 | 2/2010 | Hariton et al. |
| 2011/0092966 | A1 | 4/2011 | Guo et al. |
| 2011/0177150 | A1 | 7/2011 | Pathak et al. |
| 2011/0214398 | A1 | 9/2011 | Liburd et al. |
| 2011/0238167 | A1 | 9/2011 | Dove et al. |
| 2011/0295363 | A1 | 12/2011 | Girard et al. |
| 2011/0300625 | A1 | 12/2011 | Paniagua et al. |
| 2011/0306124 | A1 | 12/2011 | Strasly et al. |
| 2011/0311493 | A1 | 12/2011 | Dove et al. |
| 2012/0035720 | A1 | 2/2012 | Cali et al. |
| 2012/0059487 | A1 | 3/2012 | Cunanan et al. |
| 2012/0067855 | A1 | 3/2012 | Guo et al. |
| 2012/0078356 | A1 | 3/2012 | Fish et al. |
| 2012/0095551 | A1 | 4/2012 | Navia et al. |
| 2012/0123557 | A1 | 5/2012 | Carpentier et al. |
| 2012/0185038 | A1 | 7/2012 | Fish et al. |
| 2012/0328905 | A1 | 12/2012 | Guo et al. |
| 2013/0122583 | A1 | 5/2013 | Neethling |
| 2013/0238088 | A1 | 9/2013 | Navia et al. |
| 2013/0243738 | A1* | 9/2013 | Griffiths .............. C12N 5/0658 |
| | | | 435/395 |
| 2015/0088247 | A1 | 3/2015 | L'Heureux et al. |
| 2017/0173214 | A1 | 6/2017 | Wang et al. |
| 2019/0374680 | A1 | 12/2019 | Lehenberger et al. |

FOREIGN PATENT DOCUMENTS

| | | | |
|---|---|---|---|
| EP | 0169259 | A1 | 1/1986 |
| EP | 2394673 | A1 | 12/2011 |
| WO | 8401894 | A1 | 5/1984 |
| WO | 9511047 | A1 | 4/1995 |
| WO | 9522361 | A1 | 8/1995 |
| WO | 9534332 | A1 | 12/1995 |
| WO | 9613227 | A1 | 5/1996 |
| WO | 9807452 | A1 | 2/1998 |
| WO | 9843556 | A1 | 10/1998 |
| WO | 0032252 | A1 | 6/2000 |
| WO | 2004082536 | A1 | 9/2004 |
| WO | 2006026325 | A2 | 3/2006 |
| WO | 2006099334 | A2 | 9/2006 |
| WO | 2011132089 | A2 | 10/2011 |
| WO | 2013009851 | A2 | 1/2013 |

OTHER PUBLICATIONS

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified And Cross-Linked Bovine Pericardium As A Ligament Substitute," Journal of Biomedical Materials Research, vol. 21, No. 12, pp. 1383-1394, 1987, University of Arizona Health Science Center, Tucson, AZ.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./ Feb. 2011.

Grabenwoger, M. et al. "Decreased Tissue Reaction to Bioprosthetic Heart Valve Material after L-glutamic acid Treatment. A Morphological Study." J. Biomed Mater. Res. Sep. 1992;26(9):1231-40.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium- Binding Amino Acid, y-Carboxyglutamate, in Mineralized Tissue," Proc. Nat. Acad. Sci, vol. 72, No. 10, pp. 3925-3929, Oct. 1975.

Jayakrishnan, A., et al., "Glutaraldehyde as a Fixative in Bioprostheses and Drug Delivery Matrices," Biomaterials, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

Liao, K., et al., "Mechanical Stress: An Independent Determinant of Early Bioprosthetic Calcification in Humans," Ann. Throac. Surg 2008;86:491-495.

Neethling, W., et al., "Enhanced Biostability and Biocompatibility of Decellularized Bovine Pericardium, Crosslinked with an Ultra-Low Concentration Monomeric Aldehyde and Treated with ADAPT®," J. Heart Valve Dis. 2008; 17: 456-464.

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Trantina-Yates AE, et al. "Detoxification of Top Enhanced, Diamine-Extended Glutaraldehyde Fixation Significantly Reduces Bioprosthetic Root Calcification in the Sheep Model," J. Heart Valve Dis. Jan. 2003; 12 (1):93-100.

Zilla, P., et al., "Carbodiimide Treatment Dramatically Potentiates the Anticalcific Effect of Alpha-Amino Oleic Acid on Glutaraldehyde-

(56)          References Cited

OTHER PUBLICATIONS

Fixed Aortic Wall Tissue," The Annals of Thoracic Surgery, Elsevier, vol. 79, No. 3, ISSN: 0003-4975; Mar. 1, 2005.

* cited by examiner

Process 100

BIOPROSTHETIC TISSUE PREPARATION

CROSS-REFERENCE TO RELATED APPLICATION

This application is a continuation of International Patent Application No. PCT/US2020/063728, filed Dec. 8, 2020, which claims the benefit of U.S. Patent Application No. 62/945,721, filed Dec. 9, 2019, the entire disclosures all of which are incorporated by reference for all purposes.

TECHNICAL FIELD

The application is generally directed to methods of preparing bioprosthetic tissue, and more specifically to methods that include removal of antigenic biomolecules and/or cells from bioprosthetic tissue, including biodegradable or non-biodegradable tissue.

BACKGROUND

Bioprosthetic tissue is utilized in a number of medical devices as an alternative to mechanical medical devices. For instance, tissue-based prosthetic heart valves can be utilized as an alternative to mechanical heart valves, each conferring their benefits and drawbacks. Mechanical heart valves have a very long life expectancy but require a patient to utilize blood thinners for the rest of their life to reduce the risk of blood clots. Patients utilizing blood thinners can have severe medical issues whenever bleeding occurs. Tissue-based heart valves typically do not require a patient to utilize blood thinners, but the tissue-based prosthetics have a shorter life expectancy (15-30 years). Thus, patients receiving tissue-based heart valves would likely need additional surgeries to replace tissue-based heart valves that have degraded. For many young patients, the decision between mechanical or tissue-based heart valves can be very difficult.

SUMMARY OF THE DISCLOSURE

Many aspects of the disclosure are directed to methods to prepare tissue for preclinical or clinical use, including remove antigenic biomolecules and/or cells from bioprosthetic tissue.

In an aspect, antigens and cells are removed from a bioprosthetic tissue. Hydrophilic biomolecules are solubilized within the bioprosthetic tissue utilizing a reducing agent. Lipophilic biomolecules are solubilized within the bioprosthetic tissue utilizing at least one detergent. Biomolecules are enzymatically degraded within the bioprosthetic tissue utilizing at least one of: nuclease, lipase, carbohydrase, or depolymerase.

In another aspect, the reducing agent is one of: β-mercaptoethanol (BME or 2-ME), tris(2-carboxyethyl)phosphine (TCEP), dithiothreitol (DTT), tributylphosphine (TBP of TnBP), or a combination thereof.

In yet another aspect, the at least one detergent is a nonionic detergent, a zwitterionic detergent, an ionic detergent, or a plurality of detergents comprising at least one nonionic detergent and at least one ionic detergent.

In a further aspect, the zwitterionic detergent is one of: amidosulfobetaine-14 (ASB-14), amidosulfobetaine-16 (ASB-16), 4-octylbenzoylamido-propyl-dimethylammonio-sulfobetaine (ASB-C8o), sulfobetaine 3-10 (SB 3-10), sulfo-betaine 3-12 (SB 3-12), sulfobetaine 3-14 (SB 3-14), sulfo-betaine 3-16 (SB 3-16), sulfobetaine 3-18 (SB 3-18), 3-[(3-cholamidopropyl)dimethylammonio]-1-propanesulfonate hydrate (CHAPS), 3-([3-cholamidopropyl]dimethylam-monio)-2-hydroxy-1-propanesulfonate (CHAPSO), non-detergent sulfobetaine 195 (NDSB-195), non-detergent sulfo-betaine 201 (NDSB-201), non-detergent sulfobetaine 211 (NDSB-211), non-detergent sulfobetaine 221 (NDSB-221), non-detergent sulfobetaine 256 (NDSB-256), or a combination thereof.

In still yet another aspect, the nonionic detergent is one of: a Tween detergent, a Triton-X detergent, n-dodecyl-β-D-maltoside (DDM), digitonin, IGEPAL CA-630, N,N-bis[3-(D-gluconamido)propyl]cholamide (BigCHAP), N,N-bis[3-(D-gluconamido)propyl]deoxycholamide (Deoxy Big CHAP), or a combination thereof.

In still yet an even other aspect, the ionic detergent is one of: sodium dodecyl sulfate (SDS), sodium deoxycholate, sodium cholate, sarkosyl, or cetyltrimethylammonium bromide (CTAB), or a combination thereof.

In yet a further aspect, the nuclease is one of: RNase A, DNase I, benzonase nuclease or a combination thereof.

In an even further aspect, the lipase is one of: triacylglyc-erol lipase, pancreatic lipase, or a combination thereof.

In yet an even further aspect, the carbohydrase is one of: amylase, arabanase, cellulose, glucanse, xylanase, or a combination thereof.

In still yet an even further aspect, the bioprosthetic tissue is animal tissue.

In still yet an even further aspect, the animal tissue is one of: pericardium, heart valve, blood vessel, small intestinal submucosa, collagen-based tissue, or elastin-based tissue.

In still yet an even further aspect, the animal tissue is one of: bovine, porcine, ovine, avian, or human.

In still yet an even further aspect, undesirable tissue is removed from the bioprosthetic tissue.

In still yet an even further aspect, the undesirable tissue is one of: adipose, venous, cartilaginous, or a combination thereof.

In still yet an even further aspect, the bioprosthetic tissue is fixed.

In still yet an even further aspect, the bioprosthetic tissue is fixed by a method selected from the group consisting of: perfusion, immersion, freezing, drying, or a combination thereof.

In still yet an even further aspect, at least one crosslinking agent is used to fix the bioprosthetic tissue.

In still yet an even further aspect, the at least one crosslinking agent is one of: formaldehyde, glutaraldehyde, paraformaldehyde, formalin, genipin, 1-ethyl-3-(3-dimeth-ylaminopropyl)carbodiimide hydrochloride (EDC), or a combination thereof.

In still yet an even further aspect, the at least one crosslinking agent includes formaldehyde, glutaraldehyde, paraformaldehyde, or formalin. And the aldehyde crosslinks within the bioprosthetic tissue are stabilized.

In still yet an even further aspect, the stabilizing aldehyde crosslinks includes treating with heat for an extended period of time.

In still yet an even further aspect, the at least one crosslinking agent includes formaldehyde, glutaraldehyde, paraformaldehyde, or formalin. And free aldehydes within the bioprosthetic tissue are capped.

In still yet an even further aspect, the capping free aldehydes includes treating with a reducing agent, an amine, or a combination thereof.

In still yet an even further aspect, e at least one cross-linking agent includes 1-ethyl-3-(3-dimethylaminopropyl) carbodiimide hydrochloride (EDC). And carboxy crosslinks within the bioprosthetic tissue are stabilized.

In still yet an even further aspect, the stabilizing carboxy crosslinks includes treating with heat for an extended period of time.

In still yet an even further aspect, an enzymatic cross-linker is used to fix the bioprosthetic tissue.

In still yet an even further aspect, the enzymatic cross-linker is one of: a transglutaminase, an oxidoreductase, or a combination thereof.

In still yet an even further aspect, a precipitating agent is used to fix the bioprosthetic tissue.

In still yet an even further aspect, the precipitating agent is one of: methanol, ethanol, propanol, acetone, or a combination thereof.

In still yet an even further aspect, free carboxyl groups within the bioprosthetic tissue are capped.

In still yet an even further aspect, the capping free carboxyl groups includes treating with 1-ethyl-3-(3-dimethylaminopropyl)carbodiimide hydrochloride (EDC).

In still yet an even further aspect, a bioburden reduction treatment is performed on the bioprosthetic tissue.

In still yet an even further aspect, the bioburden reduction treatment includes one of: treatment with cytotoxic reagents, treatment with antimicrobial agents, heat treatment, pressure treatment, radiation treatment, treatment with a detergent, treatment with a crosslinking agent, or a combination thereof.

In still yet an even further aspect, the bioprosthetic tissue is stored within a solution.

In still yet an even further aspect, the solution is a fixation buffer or propylene oxide in water.

In still yet an even further aspect, the bioprosthetic tissue is treated with a solution for dry storage.

In still yet an even further aspect, the solution for dry storage includes a glycerol, polyethylene glycol, or a saccharide.

In still yet an even further aspect, the solvent for the solution for dry storage is aqueous based or alcohol based.

In still yet an even further aspect, glycerolization is performed as the treatment of the bioprosthetic tissue for dry storage.

In still yet an even further aspect, the solution for dry storage includes a percentage of glycerol selected from about: 50%, 60%, 70%, 80%, 90%, or 100%.

In still yet an even further aspect, the solution for dry storage includes a percentage of $C_1$-$C_3$ alcohol selected from about: 0%, 10%, 20%, 30%, 40%, or 50%.

In still yet an even further aspect, the bioprosthetic tissue is sterilized.

In still yet an even further aspect, the sterilizing includes a treatment selected from the group consisting of: gamma irradiation, gas plasma, aldehydes, ethylene oxide, e-beam, and a combination thereof.

In still yet an even further aspect, the bioprosthetic tissue is shaped.

In still yet an even further aspect, the shaping includes one of: die cutting, laser cutting, folding, forming, and a combination there of.

In still yet an even further aspect, the prosthetic tissue is utilized in the manufacture of a medical device.

In still yet an even further aspect, the medical device is one of: a tissue patch, a medical vessel, a conduit, a closure device, or a heart valve.

In still yet an even further aspect, the medical device is a heart valve and the prosthetic tissue is utilized to form leaflets.

Additional aspects and features are set forth in part in the description that follows, and in part will become apparent to those skilled in the art upon examination of the specification or may be learned by the practice of the various aspects described. A further understanding of the nature and advantages of the present disclosure may be realized by reference to the remaining portions of the specification and the drawings, which forms a part of this disclosure.

BRIEF DESCRIPTION OF THE DRAWINGS

The description and claims will be more fully understood with reference to the following figures, which are presented as exemplary description and should not be construed as a complete recitation of the scope of the disclosure.

DETAILED DESCRIPTION

Figure 1:
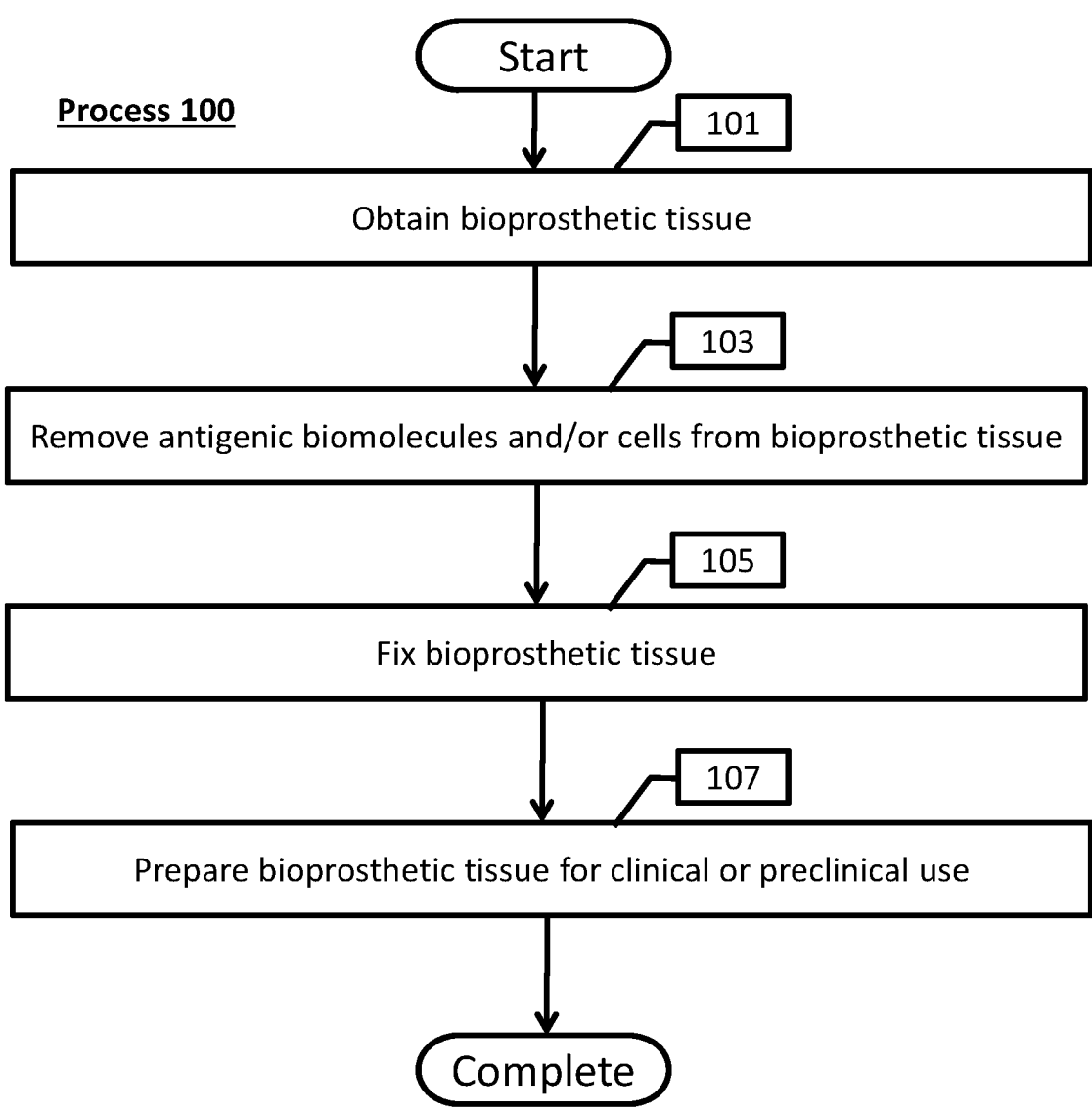
FIG. 1 provides a flow chart to prepare bioprosthetic tissue for clinical use in accordance with an aspect of the disclosure.

Turning now to the drawings and description, various methods to prepare bioprosthetic tissue are described. In several instances, bioprosthetic tissue is prepared for clinical or preclinical use, including (but not limited to) for grafting or incorporation into a medical device. In some instances, bioprosthetic tissue is prepared to be incorporated into a prosthetic heart valve, including (but not limited to) an aortic, a mitral, a tricuspid, or a pulmonary heart valve.

Aspects of the description are directed to removal of biomolecules (e.g., nucleic acids, lipids, carbohydrates, and proteins) from bioprosthetic tissue during the preparation process. It is now understood that a number of biomolecules within bioprosthetic tissue may produce an immune response in a patient that receives the bioprosthetic tissue. For example, a patient receiving a heart valve that incorporates bioprosthetic tissue may have an immune response to the bioprosthetic tissue recognizing the bioprosthetic tissue as foreign (e.g., tissue that was not naturally grown within the patient). This response is similar to an immune response against bacteria and/or an autoimmune response. When the immune system recognizes a foreign substance, the substance is referred to as an antigen the immune system tries to remove it. Accordingly, when bioprosthetic tissue induces an immune response, the bioprosthetic tissue is attacked by the immune cells which can lead to degradation of the bioprosthetic tissue. This immune response can lead to a short lifetime of many implanted medical devices that incorporate bioprosthetic tissue. Thus, in accordance with several aspects of the disclosure, it is a goal to mitigate an immune response against medical devices that incorporate bioprosthetic tissue in order prolong the device lifetime and prevent the patient from requiring additional surgeries to replace the device. As is described within, several aspects are directed to mitigating an immune response against a medical device by reducing and/or removing antigenic biomolecules and cells that may exist within bioprosthetic tissue.

Methods of Preparing Bioprosthetic Tissue

Several aspects are directed towards methods to prepare a bioprosthetic tissue for use in a medical application, including clinical and preclinical procedures. Bioprosthetic tissue, in accordance with several aspects, is animal tissue that is to be used in a medical device and/or medical procedure. Examples of bioprosthetic tissue include (but are not limited to) animal pericardium, heart valve, blood vessel, small intestinal submucosa (SIS), collagen-based tissue, and elastin-based tissue. Bioprosthetic tissue can be derived from any appropriate animal source, including (but not limited to) bovine, porcine, ovine, avian, and human donor. In many instances, bioprosthetic tissue is from a nonautologous (e.g., non-self) source, but an autologous (e.g., self) source can be utilized in accordance with some aspects of the disclosure. In many instances, bioprosthetic tissue is processed and prepared for clinical use, which may include removal of antigenic biomolecules and cells. In some instances, a processed bioprosthetic tissue is nonbiodegradable. In some instances, a processed bioprosthetic tissue is biodegradable.

In accordance with several aspects, antigenic biomolecules are any biomolecule within bioprosthetic tissue capable of producing an immunological response in a patient that receives the bioprosthetic tissue. In many instances, antigenic biomolecules include (but are not limited to) antigenic proteins, antigenic lipids, antigenic metabolites, and antigenic nucleic acids.

Provided in FIG. 1 is an exemplary process to prepare bioprosthetic for clinical or preclinical use. Process 100 begins by obtaining 101 bioprosthetic tissue. Bioprosthetic tissue can be derived from any appropriate animal source, including (but not limited to) bovine, porcine, ovine, avian, and human donor. In many instances, bioprosthetic tissue is from a nonautologous (e.g., non-self) source, but an autologous (e.g., self) source can be utilized in accordance with some applications of the method.

In some applications, a tissue is processed after retrieval from a source to remove undesirable tissue. For example, adipose, venous, cartilaginous, and/or any other undesirable tissue may be removed.

Process 100 also removes 103 antigenic biomolecules and/or cells from bioprosthetic tissue. In many instances, antigenic biomolecules that are removed include (but are not limited to) antigenic proteins, antigenic lipids, antigenic metabolites, and antigenic nucleic acids. A number of means can be utilized to remove antigenic biomolecules, including (but not limited to) treating with detergents, treating with reducing agents, treating with enzymes that hydrolyze or break down biomolecules (e.g., nucleases, lipases, carbohydrases, depolymerases).

Process 100 also fixes 105 and/or preserves bioprosthetic tissue. A number of methodologies and reagents can be utilized to fix and preserve bioprosthetic tissue. In several instances, tissue is fixed by perfusion, immersion, freezing, drying, or a combination thereof. A number of fixative reagents can be utilized, including crosslinking reagents and precipitating reagents. Crosslinking reagents include (but are not limited to) formaldehyde, glutaraldehyde, paraformaldehyde, formalin, other aldehydes, genipin, 1-ethyl-3-(3-dimethylaminopropyl)carbodiimide hydrochloride (EDC), and enzymatic crosslinkers. In some instances, an amine crosslinking reagent is utilized, such as (for example) formaldehyde, glutaraldehyde, paraformaldehyde, formalin or genipin. In some instances, a carboxy crosslinking reagent is utilized, such as (for example) EDC, which may reduce calcification of free carboxy groups. In some instances, an amine and a carboxy crosslinking are each utilized, which can be utilized concurrently or in tandem.

In some instances, bioprosthetic tissue is fixed utilizing a biodegradable crosslinker, such as (for example) an enzymatic crosslinker, which can increase biocompatibility of the tissue. Enzymatic crosslinkers include transglutaminases (e.g., factor XIII) and oxidoreductases (e.g., tyrosinases, laccases with peroxidases, and lysyl oxidases with amine oxidases). For more examples of enzymatic crosslinkers, see J. C. Schense and J. A. Hubbell, *Bioconjug Chem.* 1999; 10(1):75-81; and T. Heck, et al, *Appl Microbiol Biotechnol.* 2013; 97(2):461-75; the disclosures of which are each incorporated herein by reference for all purposes. In some instances, a biodegradable crosslinker is used instead of chemical crosslinking reagents allows the crosslinked tissue to remain biodegradable. In some applications, biodegradable tissue is used as a temporary implant and allows native tissue to grow in and replace the biodegradable tissue. In some instances, crosslinking is performed utilizing bio-orthogonal anchor and difunctional linking compounds, such as those described in in U.S. Pat. No. 9,925,303 by Benton, the disclosure of which is incorporated herein by reference for all purposes.

In some instances, a precipitating reagent is utilized. Precipitating reagents include (but are not limited to) methanol, ethanol, propanol, and acetone. The appropriate fixation methodology and reagents utilized can vary and are often dependent on the end-product. For instance, when fixed (or cross-linked) tissues are to be utilized for a clinical application, it may be desired to use a less toxic fixative or a fixative that can be rendered less toxic with a post-fixation procedure.

Process 100 further prepares 107 bioprosthetic tissue for clinical or preclinical use. The exact preparation depends on the clinical or preclinical application. In some instances, bioprosthetic tissue is utilized in the manufacture of a medical device. In some particular instances, bioprosthetic tissue is utilized to in the manufacture of heart valve. In some instances, bioprosthetic tissue is utilized in a grafting procedure. In some instances, bioprosthetic tissue is utilized in a vasculature prosthesis. In some instances, bioprosthetic tissue is used in treatment of patient. In some instances, bioprosthetic tissue used in preclinical applications, such as (for example) training procedures on cadavers, animal models, or anthropomorphic phantoms.

A number of measures can be taken to prepare bioprosthetic tissue for clinical or preclinical use. In some instances, bioprosthetic tissue is washed and/or perfused to remove harmful fixatives and other chemicals. In some instances, bioprosthetic tissue is cut, folded, and/or formed into the desired shape. In some instances, bioburden reduction (e.g., microorganismal removal and inhibition) is performed on bioprosthetic tissue. In some instances, free aldehydes within bioprosthetic tissue are capped (e.g., a chemical procedure to modify free aldehydes to prevent them from binding calcium in a host recipient).

In some instances, prosthetic tissue is prepared for storage, which may help with long-term preservation. Storage can be dry storage or wet storage. Wet storage methods include storing the tissue within a solution, such as (for example) a fixation buffer (e.g., glutaraldehyde buffer) or propylene oxide in water. Dry storage methods include treating a tissue with a solution inclusive of a biocompatible molecule for a period of time, which can allow the components of the solution to equilibrate within the tissue. The tissue is then stored free of liquids, except for the components of the aqueous solution equilibrated therein. Biocompatible molecules to be included within a solution for dry storage include (but are not limited to) glycerol, propylene glycol, polyethylene glycol, and saccharides. Solvents for dry storage include (but are not limited) aqueous based solvents, alcohol based solvents, any other biocompatible solvent, and any solvent mixture thereof. For more description of dry storage methods, see U.S. Pat. No. 6,534,004 by Chen et al., U.S. Pat. No. 8,007,992 by Tian et al., and U.S. Pat. No. 10,383,978 by Dong et al., the disclosures of which are each incorporated herein by reference for all purposes. In some instances, prosthetic tissue is sterilized, which can be performed using gamma irradiation, gas plasma, aldehydes, ethylene oxide, and/or e-beam.

A number of tissue preparation procedures have been described, including the descriptions within the following publications: U.S. Pat. No. 7,972,376 by Dove et al., U.S. Pat. No. 8,748,490 by Dove et al., U.S. Pat. No. 9,029,418 by Dove et al., U.S. Pat. No. 9,320,830 by Dove et al., U.S. Pat. No. 10,722,613 by Ashworth et al., U.S. Pub. No. 2017/0173214 by Wang, et al., and U.S. Pub. No. 2019/0374680 by Lehenberger, et al., the disclosures of which are each incorporated herein by reference for all purposes.

While specific examples of antigen removal and decellularization, fixation, and preparation of bioprosthetic tissue are described above, one of ordinary skill in the art can appreciate that various steps of the process can be performed in different orders and that certain steps may be optional according to some aspects of the description. As such, it should be clear that the various steps of the process could be used as appropriate to the requirements of specific applications. Furthermore, any of a variety of processes for antigen removal and decellularization, fixation, and preparation of bioprosthetic tissue appropriate to the requirements of a given application can be utilized in accordance with various aspects of the description.

Methods to Remove Antigenic Biomolecules

A number of aspects of the description are directed to methods of removing antigenic biomolecules and/or cells from prosthetic tissue. As it is now understood, antigens within prosthetic tissue can stimulate host immune systems, which in turn promotes degeneration of prosthetic tissue and eventual failure of the tissue. Often, prosthetic tissue grafts and/or medical devices incorporating prosthetic tissue require replacement around every 5 to 20 years. Accordingly, in a variety of instances, antigen removal from prosthetic tissue mitigates a host's immune response and mitigates degeneration of the tissue. Furthermore, in some instances, antigen removal prolongs the life expectancy of a graft or medical device, which in turn may reduce the need to replace a graft or medical device.

In several instances, antigens are removed from a prosthetic tissue utilizing detergents, reducing agents, and/or enzymes. In numerous instances, antigens to be removed are biomolecules including (but not limited to) proteins, lipids, nucleic acids, and carbohydrates.

Figure 2:
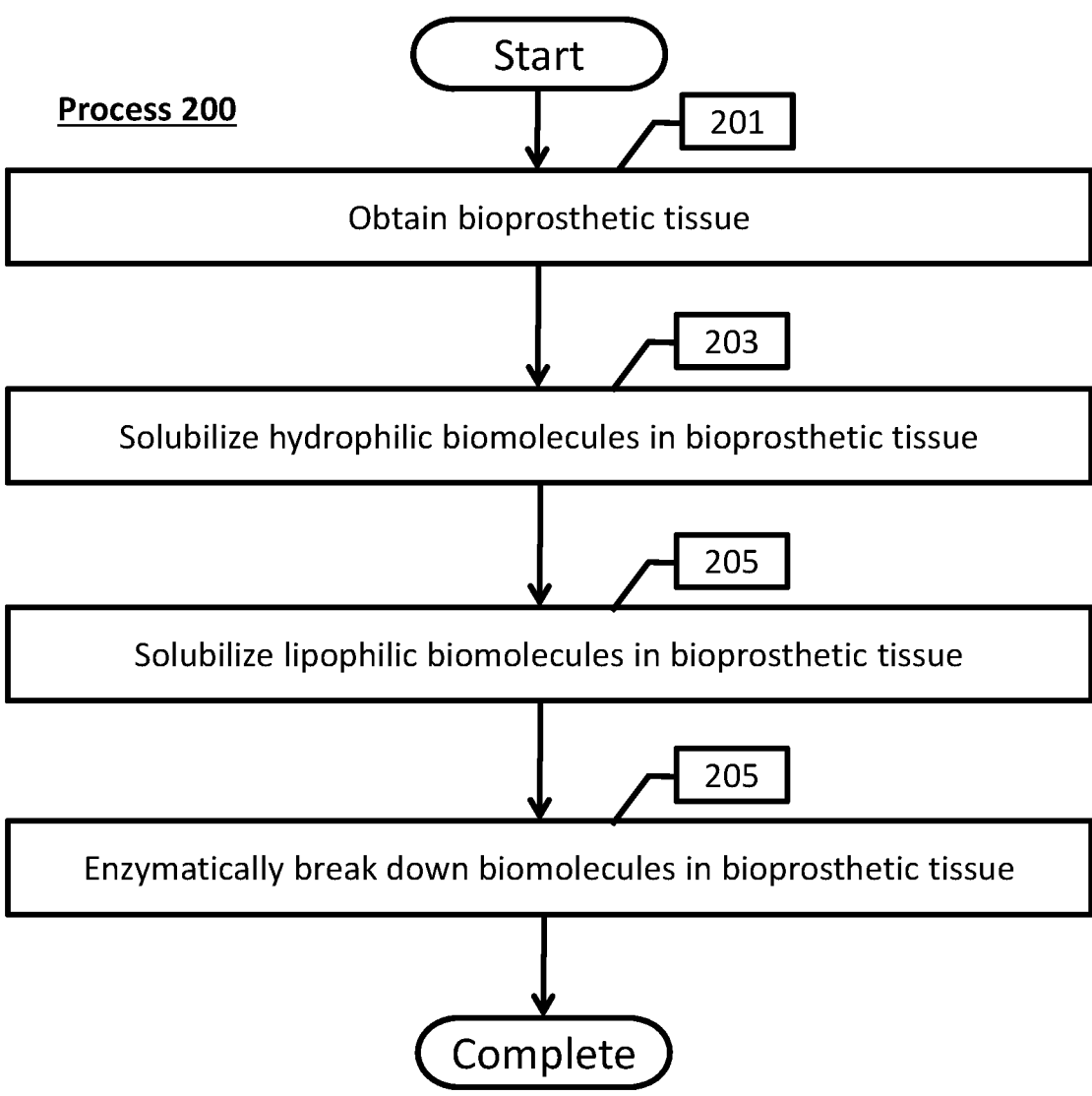
FIG. 2 provides a flow chart to remove antigenic biomolecules and/or cells from bioprosthetic tissue in accordance with an aspect of the disclosure.

Provided in FIG. 2 is an exemplary process of a method to remove antigenic biomolecules. Process 200 begins with obtaining 201 bioprosthetic tissue. Bioprosthetic tissue can be derived from any appropriate animal source, including (but not limited to) bovine, porcine, ovine, avian, and human donor. In many instances, bioprosthetic tissue is from a nonautologous (e.g., non-self) source, but an autologous (e.g., self) source can be utilized in accordance with some aspects of the description.

In some instances, a tissue is processed after retrieval from a source to remove undesirable tissues. For example, adipose, venous, cartilaginous, and/or any other undesirable tissue may be removed. In some instances, a destabilizing or depolymerization agent is utilized.

Process 200 solubilizes 203 hydrophilic biomolecules in bioprosthetic tissue. Solubilization of hydrophilic biomolecules results in their release from bioprosthetic tissue, which in turn can be removed by rinsing, washing, perfusion and/or other appropriate method to remove soluble components. In many instances, hydrophilic biomolecules to be solubilized are any water soluble biomolecules that exist within bioprosthetic tissue, including (but not limited to) cytosolic proteins, extracellular proteins, polysaccharides, oligosaccharides, monosaccharides, metabolites, amino acids, nucleic acid oligomers and monomers and other biomolecules soluble in the cytosolic or extracellular space of the tissue.

In several instances, solubilization of hydrophilic biomolecules is achieved by utilizing a detergent, a reducing agent, an enzyme to break down hydrophilic molecules, or a combination thereof. In numerous instances, at least one reducing agent is utilized. Reducing agents that can be utilized include (but are not limited to) $\beta$-mercaptoethanol (BME or 2-ME), tris(2-carboxyethyl)phosphine (TCEP), dithiothreitol (DTT), tributylphosphine (TBP or TnBP), and combinations thereof.

In many instances, solubilization of hydrophilic biomolecules is performed in an aqueous solution. In some instances, an aqueous solution is buffered to maintain a pH below about 8.5, and in some instances a pH between about 7.5 and 8.5, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Solubilization of hydrophilic biomolecules can be performed in any appropriate temperature to confer appropriate activity including (but not limited to) room temperature (~25° C.), and body temperature (~37° C.). The duration of hydrophilic solubilization can be performed to the needs of the application, depending on the reagents utilized, temperature, and desired results. In some instances, bioprosthetic tissue is treated with a hydrophilic solubilization solution for about: 1 hour, 2 hours, 4 hours, 8 hours, 12 hours, 24 hours, 48 hours, 72 hours, or greater than 72 hours.

Process 200 also solubilizes 205 lipophilic biomolecules in bioprosthetic tissue. Solubilization of lipophilic biomolecules results in their release from bioprosthetic tissue, which in turn can be removed by rinsing, washing, perfusion and/or other appropriate method to remove lipid soluble components. In many instances, lipophilic biomolecules to be solubilized are any lipid soluble biomolecules that exist within bioprosthetic tissue, including (but not limited to) phospholipids, transmembrane proteins, cholesterol, nuclear pores, and other biomolecules soluble in the membranous portions of the tissue.

In several instances, solubilization of lipophilic biomolecules is achieved by utilizing a detergent, reducing agent, an enzyme to break down lipophilic molecules, or a combination thereof. In numerous instances, at least one reducing agent is utilized. Reducing agents include (but are not limited to) $\beta$-mercaptoethanol (BME or 2-ME), tris(2-carboxyethyl)phosphine (TCEP), dithiothreitol (DTT), tributylphosphine (TBP or TnBP), and combinations thereof. In numerous instances, at least one detergent is utilized. In some instances, the at least one detergent is a zwitterionic detergent. In some instances, the at least one detergent is a nonionic detergent. In some instances, the at least one detergent is an ionic detergent. In some instances, a nonionic and an ionic detergent are utilized concurrently. In some instances, a nonionic and a zwitterionic detergent are utilized concurrently. In some instances, an ionic and a zwitterionic detergent are utilized concurrently. In some instances, a nonionic, an ionic and a zwitterionic detergent are utilized concurrently. Zwitterionic detergents include (but are not limited to) amidosulfobetaine-14 (ASB-14), amidosulfobetaine-16 (ASB-16), 4-octylbenzoylamido-propyl-dimethylammoniosulfobetaine (ASB-C8o), sulfobetaine 3-10 (SB 3-10), sulfobetaine 3-12 (SB 3-12), sulfobetaine 3-14 (SB 3-14), sulfobetaine 3-16 (SB 3-16), sulfobetaine 3-18 (SB 3-18), 3-[(3-cholamidopropyedimethylammonio]-1-propanesulfonate hydrate (CHAPS), 3-([3-cholamidopropyl]dimethylammonio)-2-hydroxy-1-propanesulfonate (CHAPSO), non-detergent sulfobetaine 195 (NDSB-195), non-detergent sulfobetaine 201 (NDSB-201), non-detergent sulfobetaine 211 (NDSB-211), non-detergent sulfobetaine 221 (NDSB-221), non-detergent sulfobetaine 256 (NDSB-256), and combinations thereof. Nonionic detergents include (but are not limited to) polysorbate non-ionic detergents (e.g. TWEEN® polysorbate detergents, Croda International), polyethelene oxide non-ionic detergents (e.g., Triton™ X polyethylene oxide non-ionic detergents, Dow Chemical), n-dodecyl-β-$\text{D}$-maltoside (DDM), digitonin, IGEPAL CA-630, N,N-Bis[3-($\text{D}$-gluconamido)propyl]cholamide (BigCHAP), and N,N-bis[3-($\text{D}$-gluconamido)propyl] deoxycholamide (Deoxy Big CHAP). Polysorbate non-ionic detergents include (but are not limited to) polysorbate 20 (e.g., TWEEN® 20) and polysorbate 80 (e.g., TWEEN® 80). Polyethelene oxide non-ionic detergents include (but are not limited to) 2-[4-(2,4,4-trimethylpentan-2-yl)phenoxy]ethanol (Triton™ X-100) and 1,1,3,3-Tetramethylbutyl)phenyl-polyethylene glycol (Triton™ X-114). Ionic detergents include (but are not limited to) sodium dodecyl sulfate (SDS), sodium deoxycholate, sodium cholate, sarkosyl, and cetyltrimethylammonium bromide (CTAB).

In many instances, solubilization of lipophilic biomolecules is performed in an aqueous solution. In some instances, an aqueous solution is buffered to maintain a pH below about 8.5, and in some instances a pH between about 7.5 and 8.5, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Solubilization of lipophilic biomolecules can be performed in any appropriate temperature to confer appropriate activity including (but not limited to) room temperature (~25° C.), and body temperature (~37° C.). The duration of lipophilic solubilization can be performed to the needs of the application, depending on the reagents utilized, temperature, and desired results. In some instances, bioprosthetic tissue is treated with a lipophilic solubilization solution for about: 1 hour, 2 hours, 4 hours, 8 hours, 12 hours, 24 hours, 48 hours, 72 hours, or greater than 72 hours.

Process 200 further enzymatically degrades (207) biomolecules in bioprosthetic tissue, especially polymeric biomolecules. Enzymatic breakdown of larger biomolecules results in these molecules to be reduced to smaller components to enhance their release from bioprosthetic tissue, which in turn can be removed by rinsing, washing, perfusion and/or other appropriate method to remove biomolecule components. In many instances, biomolecules to be enzymatically broken down are any larger biomolecules existing within bioprosthetic tissue that are difficult to remove, including (but not limited to) nucleic acids including DNA and RNA, protein complexes, cytoskeletal components including microfilaments, microtubules, and intermediate filaments, and other macro-sized biomolecules within the tissue. In a variety of instances, enzymes utilized to break down biomolecules include (but are not limited to) nucleases (e.g., RNase A, DNase, Benzonase), lipases (e.g., triacylglycerol lipase and pancreatic lipase), carbohydrases (e.g., amylase, arabanase, cellulase, glucanase, and xylanase) and depolymerases (e.g., Cytochalasin A, Cytochalasin B, Cytochalasin C, Cytochalasin D, Cytochalasin E, Cytochalasin F, Cytochalasin G, Cytochalasin H, Cytochalasin I, Cytochalasin J, Swinholide A, Scytophycin A, Scytophycin B, Scytophycin E, Mycalolide A, Mycalolide B, and Mycalolide C).

In many instances, enzymatic breakdown of lipophilic biomolecules is performed in an aqueous solution suitable for the enzymatic activity. In some instances, an aqueous solution is buffered to maintain a pH above 8.0 and below about 8.5, and in some instances a pH between about 6.5 and 7.5, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Enzymatic breakdown of biomolecules can be performed in any appropriate temperature to confer appropriate activity including (but not limited to) room temperature (~25° C.) and body temperature (~37° C.). The duration of enzymatic breakdown can be performed to the needs of the application, depending on the reagents utilized, temperature, and desired results. In some instances, bioprosthetic tissue is treated with an enzyme for about: 1 hour, 2 hours, 4 hours, 8 hours, 12 hours, 24 hours, 48 hours, 72 hours, or greater than 72 hours.

While specific examples of antigen removal of bioprosthetic tissue are described above, one of ordinary skill in the art can appreciate that various steps of the process can be performed in different orders and that certain steps may be optional according to some aspects of the disclosure. For example, the order of hydrophilic solubilization, lipophilic solubilization, and enzymatic break down can each occur in any particular order and/or be removed and/or combined. In some instances, hydrophilic solubilization and lipophilic solubilization are performed concurrently. As such, it should be clear that the various steps of the process could be used as appropriate to the requirements of specific applications. Furthermore, any of a variety of processes for antigen removal and decellularization of bioprosthetic tissue appropriate to the requirements of a given application can be utilized in accordance with various aspects of the description.

Methods to Assemble and Prepare Medical Devices

Several aspects of the description are directed to methods of utilizing antigen removed and decellularized and/or fixed bioprosthetic tissue to be incorporated within medical devices. In many instances, a medical device is any prosthetic device for the purpose of implanting into a recipient. Recipients include (but are not limited to) patients, animal models, cadavers, or anthropomorphic phantoms. In a number of instances, a medical device is a tissue patch, a medical vessel, a conduit, a closure device, or a prosthetic heart valve including (but not limited to) aortic, mitral, tricuspid and pulmonary prosthetic valves. A number of treatments can be performed on bioprosthetic tissue to prepare it for clinical or preclinical use, including (but not limited to) antigen removal and decellularization, tissue fixation, tissue stabilization, bioburden reduction, cutting and shaping of tissue, assembly into a medical device, preservation, sterilization, and any set of combinations thereof.

Figure 3:
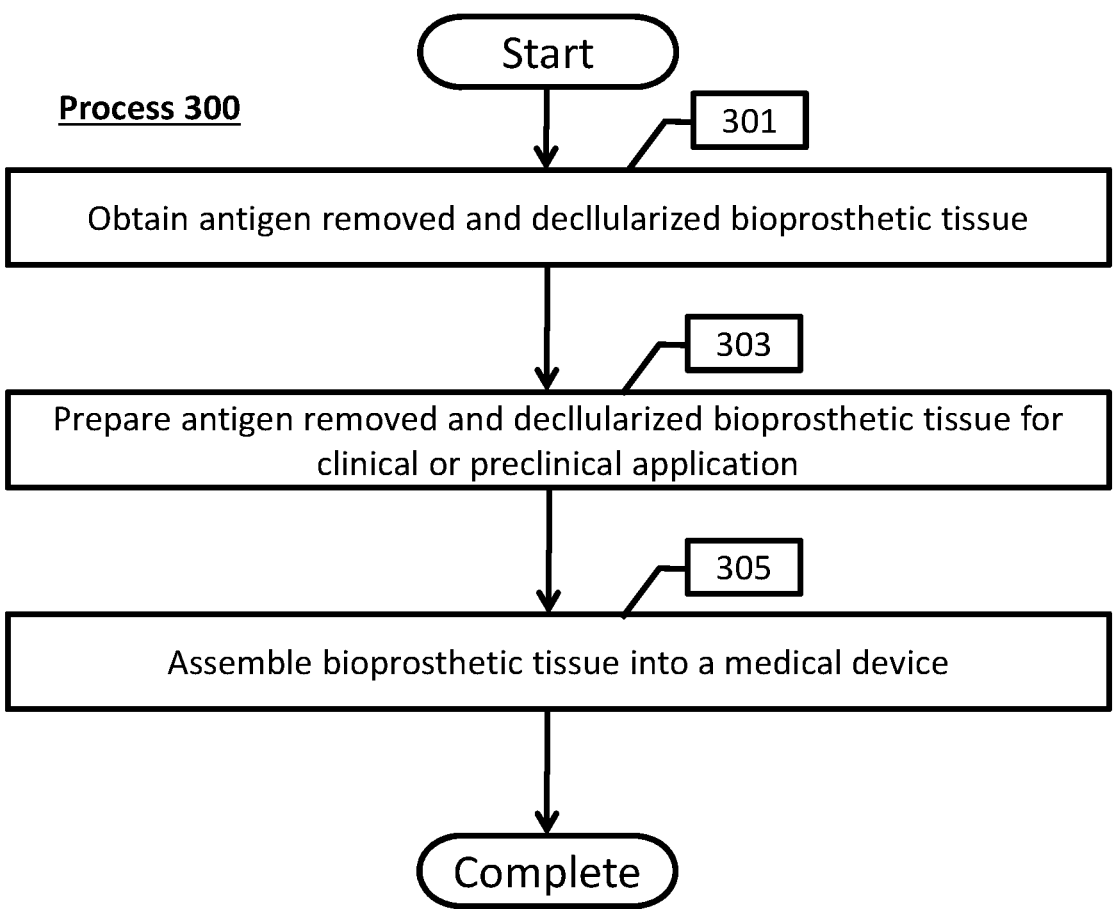
FIG. 3 provides a flow chart to prepare bioprosthetic tissue for assembly into a medical device in accordance with an aspect of the disclosure.

Provided in FIG. 3 is an exemplary process of a method to assemble a medical device utilizing antigen-removed and decellularized bioprosthetic tissue and prepare the device for clinical or preclinical use. Process 300 begins with obtaining 301 antigen removed and decellularized bioprosthetic tissue. Bioprosthetic tissue can be derived from any appropriate animal source, including (but not limited to) bovine, porcine, ovine, avian, and human donor. In many instances, bioprosthetic tissue is from a nonautologous (e.g., non-self) source, but an autologous (e.g., self) source can be utilized in accordance with some aspects of the description.

In some instances, a tissue is processed to remove undesirable tissue after retrieval from a source and prior to antigen removal and decellularization. For example, adipose, venous, cartilaginous, and/or any other undesirable tissue may be removed. In some instances, a stabilizing or depolymerization agent is utilized.

In a variety of instances, antigenic biomolecules are removed, including but not limited to antigenic proteins, antigenic lipids, antigenic metabolites, and antigenic nucleic acids. A number of means can be utilized to remove antigenic biomolecules, including (but not limited to) treating with detergents, treating with reducing agents, treating with enzymes that hydrolyze or break down biomolecules (e.g., nucleases, lipases, carbohydrases, depolymerases). In some instances, antigenic biomolecules are removed as described in FIG. 2.

Process 300 also prepares 303 antigen removed and decellularized bioprosthetic tissue for clinical or preclinical use. A number of treatments can be performed, including (but not limited to) tissue fixation, tissue stabilization, bioburden reduction, cutting and shaping of tissue, preservation, sterilization, and any set of combinations thereof. It is noted that many, if not all treatments can be performed prior to, subsequent of, or both prior to and subsequent of antigen removal.

In a number of instances, bioprosthetic tissue is fixed and/or crosslinked. In a variety of instances, tissue is fixed by perfusion, immersion, freezing, drying, or a combination thereof. A number fixative reagents can be utilized, including (but not limited to) crosslinking reagents and precipitating reagents. In several instances, bioprosthetic tissue is fresh (e.g., has not been fixed). In some instances, bioprosthetic tissue is enzymatically crosslinked.

In many instances, crosslinking fixation is performed in a suitable aqueous solution. In several instances, a crosslinking reagent is utilized in an active concentration of between about 0.1% and 1.5% (w/v), as dependent on the reagent. For example, glutaraldehyde can be used at about a concentration of \$0.5% to 1.5%; genipin can be used at about a concentration of 0.1% to 1.0%; and EDC can be used at about 1 mmol/g of tissue to 10 mmol/g of tissue. In some instances, an amine crosslinking reagent is utilized, such as (for example) formaldehyde, glutaraldehyde, paraformaldehyde, formalin or genipin. In some instances, a carboxy crosslinking reagent is utilized, such as (for example) EDC, which may reduce calcification of free carboxy groups. In some instances, an amine and a carboxy crosslinking are each utilized, which can be utilized concurrently or in tandem. In some instances, an aqueous solution is buffered to maintain a pH below about 8.5, and in some instances a pH between about 7 and 8, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Crosslinking fixation can be performed in any appropriate temperature to confer appropriate activity including (but not limited to) room temperature (~25° C.) and body temperature (~37° C.). The duration of treatment can be performed to the needs of the application, depending on the reagents utilized, temperature, and desired results. In some instances, bioprosthetic tissue is treated for about: 48 hours, 96 hours, 168 hours, 336 hours, 504 hours, or greater than 504 hours.

In many instances, enzymatic crosslinking is performed in a suitable aqueous solution, which can increase biocompatibility of the tissue. Enzymatic crosslinkers include transglutaminases (e.g., factor XIII) and oxidoreductases (e.g., tyrosinases, laccases with peroxidases, and lysyl oxidase with amine oxidases). In some instances, an aqueous solution is buffered to maintain a pH below about 8.5, and in some instances a pH between about 6.5 and 7.5, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Enzymatic crosslinking of biomolecules can be performed in any appropriate temperature to confer appropriate activity including (but not limited to) room temperature (~25° C.) and body temperature (~37° C.). The duration of enzymatic crosslinking can be performed to the needs of the application, depending on the reagents utilized, temperature, and desired results. In some instances, bioprosthetic tissue is treated with an enzyme for about: 1 hour, 2 hours, 4 hours, 8 hours, 12 hours, 24 hours, 48 hours, 72 hours, or greater than 72 hours.

In some instances, a bioburden reduction treatment is performed on bioprosthetic tissue. Bioburden reduction is a treatment to remove, eliminate, or mitigate the load of microorganisms that may exist within, on, or surrounding bioprosthetic tissue. Bioburden reduction can be performed by a number of means, including (but not limited to) treating with cytotoxic reagents (e.g., ethanol and sodium hypochlorite), antimicrobial agents (e.g., antibiotics, fungicide, antiviral agents), heat, pressure, radiation (e.g., UV irradiation), detergents (e.g., sodium dodecyl sulfate, tween 20), crosslinking agents (e.g., formaldehyde, glutaraldehyde, and/or EDC), and combinations thereof.

In many instances, bioburden reduction is performed in a suitable aqueous solution. In some instances, an aqueous solution is buffered to maintain a pH below about 8.5, and in some instances a pH between about 6.5 and 7.5, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Bioburden reduction can be performed in any appropriate temperature to confer appropriate activity including (but not limited to) room temperature (~25° C.) and body temperature (~37° C.). The duration of treatment can be performed to the needs of the application, depending on the reagents utilized, temperature, and desired results. In some instances, bioprosthetic tissue is treated for about: 1 hour, 2 hours, 4 hours, 8 hours, 12 hours, 24 hours, 48 hours, 72 hours, or greater than 72 hours.

In some instances, a crosslinking stabilization is performed on crosslinked bioprosthetic tissue. Crosslinking stabilization is a treatment to further stabilize a fixation process performed on a bioprosthetic tissue. Crosslinking stabilization can be performed by a number of means, including (but not limited to) treating with heat for extended periods of time. In some instances utilizing heat treatment, bioprosthetic tissue is kept in the presence of the crosslinking agent (e.g., formaldehyde, glutaraldehyde, and/or EDC) at a concentration between about 0.5% and 1.5% (w/v). In some instances utilizing heat treatment, the crosslinking agent (e.g., formaldehyde, glutaraldehyde, and/or EDC) is not utilized.

In many instances, crosslinking stability is performed in a suitable aqueous solution. In some instances, an aqueous solution is buffered to maintain a pH below about 8.5, and in some instances a pH between about 5.5 and 6.5, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Stabilization of crosslinking can be performed in any appropriate temperature to confer appropriate stabilization including (but not limited to) ~40° C., ~50° C., ~60° C., or ~70° C. It is important that the increased temperature is not too high such that the tissue is damaged. The duration of stabilization can be performed to the needs of the application, depending on the reagents utilized, temperature, and desired results. In some instances, bioprosthetic tissue is treated with an enzyme for about: 24 hours, 48 hours, 72 hours, 96 hours, 120 hours, 144, 168 hours, or greater than 168 hours.

In some instances, an aldehyde capping treatment is performed on bioprosthetic tissue that has been fixed with an aldehyde. Aldehyde capping is a treatment to reduce the amount of free aldehydes within a crosslinked bioprosthetic tissue such that calcification is mitigated when transplanted into a receiving patient. Aldehyde capping can be performed by a number of means, including (but not limited to) treating with reducing agents or amine molecules. For more on aldehyde capping, see U.S. Pat. No. 7,972,376 by Dove et al., U.S. Pat. No. 8,748,490 by Dove et al., U.S. Pat. No. 9,029,418 by Dove et al., and U.S. Pat. No. 9,320,830 by Dove et al., the disclosures of which are each incorporated herein by reference for all purposes.

In some instances, a carboxy capping treatment is performed on bioprosthetic tissue. Carboxy capping is a treatment to reduce the amount of free carboxyl groups within a bioprosthetic tissue such that calcification is mitigated when transplanted into a receiving patient. Capping of carboxyl groups can be performed by a number of means, including (but not limited to) treating with EDC. For more on carboxy capping, see U.S. Pat. No. 9,878,068 by Davidson et al., the disclosure of which is incorporated herein by reference for all purposes.

In many instances, aldehyde and/or carboxy capping is performed in a suitable aqueous solution. In some instances, an aqueous solution is buffered to maintain a pH below about 8.5, and in some instances a pH between about 6.5 and 7.5, which may confer a benefit to stabilize the aqueous environment and the bioprosthetic tissue. Any appropriate buffer salt may be utilized, including (but not limited to) phosphate buffered solution (PBS), potassium chloride (KCl), monobasic potassium phosphate ($KH_2PO_4$), dibasic potassium phosphate ($K_2HPO_4$), sodium chloride (NaCl) including isotonic saline, potassium bromide (KBr), sodium bromide (NaBr), calcium chloride ($CaCl_2$), HEPES, MES, MOPS, HEPPs, HEPBS, and Tris-HCl. Aldehyde and/or carboxy capping can be performed in any appropriate temperature to confer appropriate activity including (but not limited to) ~4° C., room temperature (~25° C.), and ~30° C. The duration of treatment can be performed to the needs of the application, depending on the reagents utilized, temperature, and desired results. In some instances, bioprosthetic tissue is treated for about: 1 hour, 2 hours, 4 hours, 8 hours, 12 hours, 24 hours, 48 hours, 72 hours, or greater than 72 hours.

In some instances, a sterilization treatment is performed on bioprosthetic tissue. Sterilization can be performed by a number of methods, including (but not limited to) gamma irradiation, gas plasma, aldehydes, ethylene oxide, e-beam, and/or computerized tomography (CT) scan.

In some instances, prosthetic tissue is prepared for storage, which may help with long-term preservation. Storage can be dry storage or wet storage. Wet storage methods include storing the tissue within a solution, such as (for example) a fixation buffer (e.g., glutaraldehyde buffer) or propylene oxide in water. Dry storage methods include treating a tissue with a solution inclusive of a biocompatible molecule for a period of time, which can allow the components of the solution to equilibrate within the tissue. The tissue is then stored free of liquids, except for the components of the aqueous solution equilibrated therein. Biocompatible molecules to be included within a solution for dry storage include (but are not limited to) glycerol, propylene glycol, polyethylene glycol, and saccharides. Solvents for dry storage include (but are not limited) aqueous based solvents, alcohol based solvents, any other biocompatible solvent, and any solvent mixture thereof. For more description of dry storage methods, see U.S. Pat. No. 6,534,004 by Chen et al., U.S. Pat. No. 8,007,992 by Tian et al., and U.S. Pat. No. 10,383,978 by Dong et al., the disclosures of which are each incorporated herein by reference for all purposes.

In many instances, glycerolization for dry storage is performed in a suitable solution. In some instances, a solution includes a percentage of glycerol. In some instances, a solution includes a percentage of glycerol and a $C_1$-$C_3$ alcohol. In some instances, the percentage of glycerol is about: 50%, 60%, 70%, 80%, 90%, or 100%. In some instances, the percentage of $C_1$-$C_3$ alcohol is about: 0%, 10%, 20%, 30%, 40%, or 50% $C_1$-$C_3$ alcohols include methanol, ethanol, i-propanol, 2-propanol, and mixtures thereof. Glycerolization can be performed in any appropriate temperature to confer appropriate activity including (but not limited to) room temperature (~25° C.) and body temperature (~37° C.). The duration of treatment can be performed to the needs of the application, depending on the reagents utilized, temperature, and desired results. In some instances, bioprosthetic tissue is glycerolized for about: 1 hour, 2 hours, 4 hours, 8 hours, 12 hours, 24 hours, 48 hours, 72 hours, or greater than 72 hours.

In some instances, bioprosthetic tissue is cut, folded, and/or formed into the desired shape. Any appropriate means to cut or shape bioprosthetic tissue can be utilized, including (but not limited to) die cutting and laser cutting.

It is to be understood that various processes to prepare antigen removed bioprosthetic tissue can be performed in any appropriate order. Furthermore, in some instances, various processes are not utilized, or are utilized more than once. For example, a rough cut of bioprosthetic tissue may be performed early in a preparation process and then further cut to a more precise shape prior to assembly within a medical device.

Returning to FIG. 3, Process 300 further assembles 305 bioprosthetic tissue into a medical device. In a number of instances, a medical device is a prosthetic heart valve including (but not limited to) aortic, mitral, tricuspid and pulmonary prosthetic valves. In various instances, bioprosthetic tissue is utilized to form vascular patches, tissue patches, conduits, pericardial patches and/or leaflets of the valve.

In several instances, after assembly of a medical device, the device incorporating can be prepared for clinical or preclinical application, which may include tissue stabilization, bioburden reduction, cutting and shaping of tissue, assembly into a medical device, preservation, sterilization, and any set of combinations thereof. Accordingly, a variety of the processes described in regard to step 303 can be performed prior to, subsequent of, or both prior to and subsequent of medical device assembly.

DOCTRINE OF EQUIVALENTS

While the above description contains many specific aspects of the disclosure, these should not be construed as limitations on the scope of the disclosure, but rather as various examples of one aspect thereof. Accordingly, the scope of the disclosure should be determined not by the aspects illustrated, but by the appended claims and their equivalents.

It is specifically noted that several processes described herein can vary, as would be understood by those skilled in the art. For instance, equivalent (or near-equivalent) processes, reagents, concentrations, temperatures, buffer salt solutions, solution pH, and treatment durations that yield a similar result, as would be anticipated by those skilled in the art, are to be covered in various aspects of the disclosure.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods and various systems and apparatuses.

What is claimed is:

1. A method to prepare bioprosthetic tissue for clinical or preclinical use, comprising:
fixing the bioprosthetic tissue;
solubilizing hydrophilic biomolecules within a bioprosthetic tissue utilizing a reducing agent;
solubilizing lipophilic biomolecules within the bioprosthetic tissue utilizing a nonionic detergent, a zwitterionic detergent, an ionic detergent, or a plurality of detergents comprising at least one nonionic detergent and at least one ionic detergent;
enzymatically degrading biomolecules within the bioprosthetic tissue utilizing at least one of: a nuclease, a lipase, a carbohydrase, or a depolymerase; and
assembling the bioprosthetic tissue into a medical device to be implanted within a recipient;
wherein fixing the bioprosthetic tissue is to be performed prior to assembling the bioprosthetic tissue into the medical device.

2. The method as in claim 1, wherein the reducing agent is one of: β-mercaptoethanol (BME or 2-ME), tris(2-carboxyethyl) phosphine (TCEP), dithiothreitol (DTT), tributylphosphine (TEP of TnBP), or a combination thereof.

3. The method as in claim 1, wherein the nonionic detergent is one of: a polysorbate nonionic detergent, a polyethylene oxide nonionic detergent, ndodecyl-β-D-maltoside (DDM), digitonin, IGEPAL CA-630, N,N-bis[3-(Dgluconamido) propyl]cholamide (BigCHAP), or N,N-bis [3-(Dgluconamido) propyl]deoxycholamide (Deoxy Big CHAP).

4. The method as in claim 1, wherein the ionic detergent is one of: sodium dodecyl sulfate (SDS), sodium deoxycholate, sodium cholate, sarkosyl, or cetyltrimethylammonium bromide (CTAB).

5. The method as in claim 1, wherein the zwitterionic detergent is one of: amidosulfobetaine-14 (ASB-14), amidosulfobetaine-16 (ASB-16), 4-octylbenzoylamido-propyl-dimethylammoniosulfobetaine (ASB-C8o), sulfobetaine 3-10 (SB 3-10), sulfobetaine 3-12 (SB 3-12), sulfobetaine 3-14 (SB 3-14), sulfobetaine 3-16 (SB 3-16), sulfobetaine 3-18 (SB 3-18), 3-[(3-cholamidopropyl)dimethylammonio]-1-propanesulfonate hydrate (CHAPS), 3-([3-cholamidopropyl]dimethylammonio)-2-hydroxy-1-propanesulfonate (CHAPSO), non-detergent sulfobetaine 195 (NDSB-195), non-detergent sulfobetaine 201 (NDSB-201), non-detergent sulfobetaine 211 (NDSB-211), non-detergent sulfobetaine 221 (NDSB-221), or non-detergent sulfobetaine 256 (NDSB-256).

6. The method as in claim 1, wherein the nuclease is one of: RNaseA, DNase I, benzonase, or a combination thereof.

7. The method as in claim 1, wherein the bioprosthetic tissue is animal tissue.

8. The method as in claim 7, wherein the animal tissue is one of: pericardium, heart valve, blood vessel, small intestinal submucosa, collagen-based tissue, or elastin-based tissue.

9. The method as in claim 7, wherein the animal tissue is one of: bovine, porcine, ovine, avian, or human.

10. The method as in claim 1, wherein fixing the bioprosthetic tissue comprises contacting with at least one crosslinking agent.

11. The method as in claim 10, wherein the at least one crosslinking agent is one of: formaldehyde, glutaraldehyde, paraformaldehyde, formalin, genipin, 1-ethyl-3-(3-dimethylaminopropyl) carbodiimide hydrochloride (EDC), or a combination thereof.

12. The method as in claim 11 further comprising stabilizing aldehyde crosslinks within the bioprosthetic tissue, wherein the stabilizing aldehyde crosslinks comprises treating with heat for an extended period of time.

13. The method as in claim 10, wherein the at least one crosslinking agent comprises formaldehyde, glutaraldehyde, paraformaldehyde, or formalin, and the method further comprising: capping free aldehydes within the bioprosthetic tissue.

14. The method of claim 13, wherein the capping free aldehydes comprises treating with a reducing agent, an amine, or a combination thereof.

15. The method claim 1, further comprising: treating the bioprosthetic tissue with a solution for dry storage.

16. The method as in claim 15, wherein the solution for dry storage comprises a glycerol, polyethylene glycol, or a saccharide.

17. The method as in claim 15, wherein the solvent for the solution for dry storage is aqueous based or alcohol based.

18. The method as in claim 16, wherein the solution for dry storage comprises a percentage of glycerol selected from about: 50%, 60%, 70%, 80%, 90%, or 100%.

19. The method of claim 1, wherein assembling the bioprosthetic tissue into a medical device comprises:

forming leaflets using the bioprosthetic tissue, wherein the leaflets are assembled into a heart valve.

20. A method to prepare a bioprosthetic tissue for clinical or preclinical use, comprising:

performing one or more of:

solubilizing hydrophilic biomolecules within a bioprosthetic tissue utilizing a reducing agent;

solubilizing lipophilic biomolecules within the bioprosthetic tissue utilizing a zwitterionic detergent; and enzymatically degrading biomolecules within the bioprosthetic tissue utilizing at least one of: a nuclease, a lipase, a carbohydrase, or a depolymerase;

fixing the bioprosthetic tissue;

treating the bioprosthetic tissue with a solution for dry storage or wet storage, wherein the solution for dry storage comprises a glycerol, polyethylene glycol, or a saccharide, wherein the solution for wet storage comprises propylene oxide;

wherein fixing the bioprosthetic tissue is to be performed before treating the biological with a solution for dry storage or wet storage.

21. A method to prepare a bioprosthetic tissue for clinical or preclinical use, comprising:

solubilizing hydrophilic biomolecules within a bioprosthetic tissue utilizing a reducing agent;

solubilizing lipophilic biomolecules within the bioprosthetic tissue utilizing a zwitterionic detergent, enzymatically degrading biomolecules within the bioprosthetic tissue utilizing at least one of: a nuclease, a lipase, a carbohydrase, or a depolymerase fixing the bioprosthetic tissue with formaldehyde, glutaraldehyde, paraformaldehyde, or formalin; and capping free aldehydes within the bioprosthetic tissue, wherein the capping free aldehydes is to be performed after fixing the bioprosthetic tissue with formaldehyde, glutaraldehyde, paraformaldehyde, or formalin.

* * * * *